Figure 1:
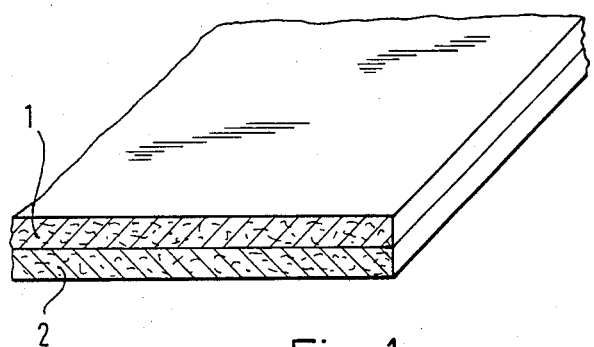

United States Patent [19]

Zimmermann et al.

[11] Patent Number: 4,606,337
[45] Date of Patent: Aug. 19, 1986

[54] RESORPTIVE SHEET MATERIAL FOR CLOSING AND HEALING WOUNDS AND METHOD OF MAKING THE SAME

[75] Inventors: Eberhard Zimmermann, Münster-Nienberge; Michael Stroetmann, Münster, both of Fed. Rep. of Germany

[73] Assignee: Serapharm GmbH & Co. KG, Muenster, Fed. Rep. of Germany

[21] Appl. No.: 486,580

[22] Filed: Apr. 19, 1983

[30] Foreign Application Priority Data

Apr. 19, 1982 [DE] Fed. Rep. of Germany ....... 3214337

[51] Int. Cl.$^4$ ............................................. A61L 15/00
[52] U.S. Cl. .................................. 128/156; 128/325; 128/334 R; 604/358; 604/368; 604/369
[58] Field of Search .......... 128/155, 156, 325, 334 R; 604/364, 368, 369, 894, 896, 897, 304, 306; 424/16, 27, 28

[56] References Cited

U.S. PATENT DOCUMENTS

| | | | |
|---|---|---|---|
| 3,698,392 | 10/1972 | Vogt et al. | 604/304 |
| 4,225,580 | 9/1980 | Rothman et al. | 424/180 |
| 4,265,233 | 5/1981 | Sugitachi et al. | 128/156 |
| 4,314,935 | 2/1982 | Uemura et al. | 424/85 |
| 4,407,787 | 10/1983 | Stemberger | 128/156 |
| 4,453,939 | 6/1984 | Zimmerman et al. | 604/368 |

*Primary Examiner*—C. Fred Rosenbaum
*Assistant Examiner*—Mario Costantino
*Attorney, Agent, or Firm*—Pollock, Vande Sande & Priddy

[57] ABSTRACT

A resorptive sheet material for closing and healing wounds substantially consists of a glycoprotein matrix containing substances which cause and, respectively, are conducive to the coagulation of blood including fibrinogen and thrombin. The sheet material is dry and of multi-layered structure, wherein at least one layer is free from thrombin and contains in the glycoprotein matrix thereof the fibrinogen in a substantially homogeneously distributed form, and at least one further layer is free from fibrinogen and contains in the glycoprotein matrix thereof the thrombin in a substantially homogeneously distributed form. The glycoproteins coming into consideration, above all, are non-linked fibrin, fibrin fission products, collagen, globulin, myoglobulin, casein and/or albumin.

Preferably, at least one of the layers, especially one or both outer layer(s), contains fibroblast cells present in dry state and/or agents conducive to the growth of the fibroblasts and their spreading-in, especially chondroitin sulphate.

For the production, fibrinogen is added to a thrombin-free, predominantly aqueous solution and/or suspension of the glycoprotein and said solution and/or suspension is processed to form a sheet-material layer, and onto the full surface of this layer at least one further layer is applied which, in its turn, has been obtained from a further, fibrinogen-free and thrombin-containing solution and/or suspension of the same or of another glycoprotein. In particular, a solution and/or suspension of one composition is applied onto an inert surface, where it is subjected to deep-freezing, and onto the resultant ice-layer surface, when still in the deep-frozen state, a solution and/or suspension of different composition is applied and subjected to deep-freezing, and, finally, all layers are jointly subjected to lyophilization.

54 Claims, 2 Drawing Figures

U.S. Patent  Aug. 19, 1986  4,606,337

RESORPTIVE SHEET MATERIAL FOR CLOSING AND HEALING WOUNDS AND METHOD OF MAKING THE SAME

The invention relates to a resorptive sheet material for closing and healing wounds, substantially consisting of a glycoprotein matrix containing substances which cause and, respectively, are conducive to the coagulation of blood including fibrinogen and thrombin.

A sheet material for healing wounds has already been known the matrix of which may consist of gelatin, collagen, polyglycolic acid or polylactic acid; this matrix material has the blood coagulation factor XIII and thrombin fixed thereto (DE-OS No. 29 14 822). This known sheet material does not contain fibrinogen.

Furthermore, a tissue adhesive, called "fibrin adhesive", has been known (cf. DE-OS No. 30 02 933) which mainly consists of a deep-frozen fibrinogen solution with additions of factor XIII and a fibrinolysis inhibitor, such as e.g. aprotinin. For practical use, the deep-frozen fibrinogen solution is thawed, a solution of thrombin and calcium chloride is added thereto, the mixture is kept for some time until the starting polymerization reaction becomes noticeable by an increase of viscosity and then this reacting mixture is applied onto the tissue parts which are to be joined. In many cases, the expenditure for preparing a tissue adhesive ready for use and the low lifetime of the preparation which is ready for use have proven to be disadvantageous.

Further, it has already been proposed (*Wiener Medizinische Wochenschrift 7"*, pp. 86-89 (1976)) to heat lyophilized fibrinogen to a temperature of 37° C., to apply the resultant solution onto a collagen fleece and to cause it to coagulate thereon by adding an aqueous solution of thrombin and an aqueous solution of factor XIII. Thereupon, the reactive sheet material is transferred onto the wound. In this case, too, the manipulation causes difficulties since the sheet material which is ready for use must be prepared directly beforehand and the short-time interval of the preparation ready for use cannot reliably be determined.

As in an aqueous medium, and even already in moist surroundings, thrombin causes the polymerization and linking of fibrinogen into fibrin, preparations which contain both thrombin and fibrinogen mostly suffer from poor storage stability.

Further, it is desirable that the sheet materials of the kind concerned contain an agent which is intended to assist in the healing of the wound.

Based thereon, it is the object of the present invention to provide a sheet material for closing and healing wounds which comprises thrombin and fibrinogen, which may be stored at ambient temperatures for prolonged periods of time without any appreciable loss of activity, and which is applied directly onto the wound, i.e. without adding further, e.g. activating components, where it is completely resorptive. According to a further objective of the invention the sheet material shall additionally contain one or more agents specifically assisting in the healing of wounds.

Furthermore, this invention provides at least a method of making such a sheet material which can be carried out easily, which in the course of production does not affect the biological activity of fibrinogen and thrombin and, where applicable, of the agent(s) specifically assisting in the healing of wounds, and which permits a wide range of variation as regards the kind, number, concentration and arrangement of the components within the sheet material.

Based on a resorptive sheet material for closing and healing wounds, substantially consisting of a glycoprotein matrix and containing substances which cause and, respectively, are conducive to the coagulation of blood including fibrinogen and thrombin, the solution of the above object, which is provided by the present invention, is characterized in that the sheet material is dry and of multi-layered structure, at least one layer of the multi-layered sheet material is free from thrombin and contains in the glycoprotein matrix thereof the fibrinogen in a substantially homogeneously distributed form; and at least one further layer of the multi-layered sheet material is free from fibrinogen and contains in the glycoprotein matrix thereof the thrombin in a substantially homogeneously distributed form.

According to a further preferred aspect of the invention at least one layer—preferably at least one of the outer layers—of the sheet material additionally contains fibroblast cells which are present in dry state.

According to a further preferred aspect of the invention at least one layer—preferably at least one of the outer layers containing thrombin and fibroblast cells—of the sheet material additionally contains one or more agents conducive to the growth and the spreading-in of fibroblast cells.

The method according to the invention for making such a sheet material provides adding fibrinogen to a thrombin-free, predominantly aqueous solution and/or suspension of the glycoprotein and processing said solution and/or suspension to form a sheet-material layer, adding thrombin to a further, predominantly aqueous fibrinogen-free solution and/or suspension of the same or of another glycoprotein and processing said solution and/or suspension to form a further sheet-material layer, and applying said layers on each other over the full surface thereof, if desired, including further, similarly prepared layers. Preferably, active fibroblast cells and/or an agent conducive to the growth as well as the spreading-in of fibroblasts is added to the thrombin containing solution and/or suspension of the glycoprotein. Preferably, chondroitin sulphate is used as the agent which is conducive to the growth and the spreading-in of fibro-blasts.

A particularly preferred embodiment of this method provides applying a solution and/or suspension of one composition of the mentioned kind onto an inert surface, where it is subjected to deep-freezing, and also deep-freezing on the resultant ice-layer surface, when still in the deep-frozen state, a further solution and/or suspension of different composition and, finally, jointly subjecting all layers to lyophilization. If desired, the applied solution and/or suspension may be foamed prior to the deep-freezing operation.

Advantageous further embodiments and modifications of the invention are apparent from the subclaims.

The invention provides a completely resorptive sheet material for closing and healing wounds, which may be stored under sterile, dry conditions at room temperature for prolonged periods of time, e.g. for two years and longer, without any appreciable loss of activity and which, after removal from its sterile package, is applied directly onto the wound and stops the haemorrhage within a short time, e.g. within approx. 2 min., due to the increased offer of biologically active thrombin and fibrinogen.

The multi-layered embodiment of the sheet material permits a spatial separation of fibrinogen and thrombin and an enrichment of components conducive to the wound healing, here especially the fibroblast growth, in at least one of the surface layers of the sheet material. This is why the storage stability is so excellent without any appreciable decrease of the biological activity. Further, the requirements as to the exclusion of moisture are not so high.

Besides, it is possible due to the multi-layered structure respectively to provide for the thrombin and the fibrinogen a particularly adapted environment. The thrombin is contained in that outer layer which is applied directly onto the wound, the so-called contact layer. Therefore, the thrombin shall be distributed in a matrix which may be rapidly soaked and which is highly stable under mechanical load in order to support the further layers. The matrix materials coming into consideration for the thrombin-containing layer preferably are plasma proteins (albumins, globulins) or fibrin fission products. The fibrinogen, on the other hand, shall be distributed in a matrix which may be incorporated into the developing fibrin network and may be rapidly decomposed physiologically. Therefore, the matrix materials preferably provided for the fibrinogen-containing layer are glycoproteins, such as collagen, non-linked fibrin or fibrin polypeptides. However, mostly such substances have a lower stability under mechanical load, e.g. a lower tear resistance or tensile strength. Therefore, according to another aspect of the invention different glycoproteins which are particularly matched to the respective requirements are provided for the various layers.

Due to the spatial separation, the common application of fibrinogen and thrombin on the support material is not necessary. Both fibrinogen and thrombin dissolve readily in water or predominantly aqueous solutions with further water-miscible solvents. The application of an aqueous solution containing both fibrinogen and thrombin is out of the question since fibrin would form from the fibrinogen and would polymerize.

However, when using a suspension of fibrinogen and thrombin in an organic solvent, there is a risk of a partial denaturing with the consequence of a loss of activity of the coagulation enzymes.

The specified multi-layered structure permits observance of precisely defined fibrinogen and thrombin quantities as well as of predetermined numbers of fibroblast cells, of which at least a fraction may be reactivated, per unit of area and/or unit of volume of the sheet material. Preferably, the fibrinogen or thrombin and, where applicable, the fibroblast cells and/or the agent conducive to the spreading-in of fibroblasts is dissolved and, respectively, distributed directly in the predominantly aqueous solution and/or suspension of the glycoprotein, which is used for the preparation of the respective layer, so that in the finished sheet material a substantially homogeneous distribution of fibrinogen and, respectively, thrombin and the further components in the respective layers is ensured. This distribution ensures a rapid and high efficiency, which cannot be achieved to the same degree e.g. in the application of a crystalline, powdery mixture of fibrinogen and thrombin on a support material.

Further, the multi-layered structure permits the application of reactive intermediate layers without any particular intrinsic mechanical stability because the outer layers ensure the stability, in particular the tensile strength of the sheet material. Finally, the multi-layered structure ensures a wide range of variation as regards the adjustment of the kind, number and/or concentration of the various components in the layers to the requirements. The method according to the invention can be carried out most easily, manages with predominantly aqueous solutions and/or suspensions and thus prevents any loss of activity of fibrinogen and thrombin and active fibroblast cells in the production. The essential components of the sheet material according to the invention have been known and may be prepared and produced according to known methods and/or obtained in specialized trade.

The sheet material consists mainly of glycoprotein of which the sheet-material layers are composed and which serves as a support material for the coagulation enzymes. The glycoprotein is to be completely resorptive and biologically decomposable since it is incorporated into the fibrin network finally covering the wound. Preferably such glycoproteins are provided as have a certain haemostatic effect already on account of their chemical nature and/or the nature of their surface, as described e.g. in respect of collagen. Animal collagen is particularly suited due to its non-antigenic properties. However, all other glycoproteins must be obtained from human material. When moistened with the exudation of a wound, the support material shall absorb the liquid, dissolve partially and form a highly viscous, sticky paste, which adheres to the wound area, withstands the pressure of the issuing blood and activates the coagulation enzymes of the contacting blood.

Within the scope of the invention, preferably non-linked fibrin, fibrin fission products, collagen, globulin, myoglobulin, casein or albumin come into consideration as glycoprotein. In certain cases, a layer is also composed of two or more of these glycoproteins.

Non-linked fibrin may be prepared from factor XIII-free fibrinogen and thrombin. An equal product is obtained in the reaction of the fibrinogen with calcium-free thrombin and cysteine for blocking the SH groups of the factor XIII. The resultant fibrin is then non-linked, may, without fiber formation, be lyophilized and pulverized and may in this form be added to a collagen solution. Fibrin fission products are prepared by the tryptic decomposition of human fibrin. After proteolysis, the material is pulverized and may be used in this form, whereby a highly water-soluble preparation is obtained.

An aqueous solution of collagen of animal origin may be obtained in specialized trade, e.g. from the company Pentapharm, Basel, Switzerland.

Suitable globulin is precipitated at a 50% ammonium sulphate concentration (i.e. one part of plasma per one part of aqueous, saturated ammonium sulphate solution) with human plasma. The product is centrifuged off, dialyzed and lyophilized.

The further suited glycoproteins, such as myoglobulin, casein and albumin, are known substances and also available in specialized trade.

What is particularly preferred as glycoproteins are collagen, collagen-like materials and fibrin fission products, which preferably form the skeleton material for the fibrinogen-containing layer, as well as non-linked fibrin and fibrin polypeptides, which preferably form the skeleton material for the thrombin-containing layer.

The layer may in different manners be composed of the glycoprotein. After the conventional preparation, various of the mentioned glycoproteins are obtained already in a leaf-like structure, as described particularly in respect of collagen and modified collagens. Such leaf structures may serve as a layer of the sheet material according to the invention after impregnation with an aqueous solution of fibrinogen or thrombin. Another possibility is to spin the glycoprotein and to produce a fleece from the resultant fibers in the wet or dry process, which fleece is then impregnated with the aqueous solution of fibrinogen or thrombin. Furthermore, the layer may have a porous foam structure. For this purpose, the glycoprotein is substantially dissolved in a predominantly aqueous solution. It is not necessary to produce a true homogeneous solution; rather, the glycoprotein may be processed also to form gel-like or gelatinous compositions. Moreover, powdery or other fine-particle glycoproteins may be present suspended and/or swelled in aqueous solution. As the solvent there is mainly used water or a solvent composition, which, apart from low amounts of water-miscible organic solvents, such as dioxan, lower glycols, ethanol, mainly consists of water.

An aqueous solution of the respective coagulation protein is added to such a predominantly aqueous solution and/or suspension of the glycoprotein, thoroughly intermixed and the mixture is then deep-frozen in an inert mold as a thin layer and lyophilized. Before the deep-freezing operation, the mixture may be foamed by means of inert foaming agents ($N_2$, $CO_2$), wherein a certain pore size may be adjusted by adding surface-active agents. A foam structure with a large surface area is obtained for the layer(s). If all layers are foamed, there will result an interengagement of adjacent layer surfaces, whereby the bond and the stability of the sheet material are increased. Preferably, the desired number of layers is built up in successive steps, and the finished layer composition is lyophilized. The product obtained thereafter may readily be pulled off the mold surface, is flexible and manipulatable without any special cautionary measures and may easily be cut, packaged and sterilized. In order to prevent a premature activation of the coagulation enzymes, the final treatment steps are to be carried out under exclusion of moisture so that a dry sheet material will be obtained and packaged moisture-proof. If required, a known drying agent, such as e.g. silica gel, may be provided within the sheet-material package and fixedly provided on the latter to keep the sheet material dry even for prolonged periods of storage.

Preferably, the sheet material according to the invention is intended for use with human beings. Therefore, the used fibrinogen preferably has been obtained from human plasma. Suitable preparations are commercially available and may be obtained e.g. from the company Bering-Werke, Marburg. Furthermore, a preparation which is well suited may be isolated according to the following process.

Human plasma is cooled to 4° C. and $\beta$-alanine (2 molar solution in ethanol) is added thereto with agitation until with further ethanol addition the raw fibrinogen precipitates. This raw fibrinogen is centrifuged off, dissolved in 0.01 M of tris buffer (pH 7.4) and again precipitated by adding 2 M of glycine. The isolated sediment is dissolved in an 0.9% aqueous NaCl solution, dialyzed relative to the same solvent, desalted and subsequently lyophilized. The resultant microcrystalline fibrinogen has a molecular weight of $340,000 \pm 5\%$, is slightly digested partially in the $\alpha$ chain, quickly dissolves after introduction into body fluid and immediately thereupon, e.g. within less than 2 min., starts to polymerize. The proportion of fibrinogen which is coagulatable in solution amounts to at least 85%. 10 parts by weight of such fibrinogen contain less than 0.1 parts by weight of cryo-insoluble globulin. It has been found that the less the amount of cryo-insoluble globulin, the more rapid the fibrin polymerization. Therefore, such a fibrinogen depleted in cryoinsoluble globulin is used preferably.

The fibrinogen content of the fibrinogen-containing layer may range from 0.1 to 30 mg, preferably from 0.5 to 10 mg per 1 $cm^3$ of glycoprotein matrix.

The thrombin provided as a further necessary coagulation enzyme serves as an initiation substance for the fibrin formation and shortens the reaction time of the fibrinogen conversion in the issuing blood. Under known, standardized conditions the thrombin shall at least have a biological activity of 10,000 international units/mg of thrombin. Suitable preparations are commercially available. E.g. a suitable thrombin in microcrystalline form having a biological activity of at least 3,000 units/mg of the preparation (which apart from thrombin comprises known stabilizers and support materials) may be obtained under the tradename "Topostasin" from Hoffmann LaRoche, Grenzach, Baden. Furthermore, part of the thrombin may be replaced by prothrombin. Prothrombin constitutes a stable thrombin store, which may be shelved for long periods of time and, in the case of access of moisture, is activitated by thrombin being present and/or the issuing blood. Prothrombin is sold e.g. as a PPSB preparation by the company Imuno-AG, Vienna. A combined preparation containing thrombin and prothrombin may e.g. be separated from a commercially available prothrombin complex by column chromatography or be extracted from human plasma by means of barium sulphate and be recovered from the crystalline precipitate.

The thrombin content including the thrombin available from prothrombin shall range from 10 to 2,000 units preferably from 50 to 1,000 units per 1 $cm^3$ of the glycoprotein matrix. These units correspond to the internationally common NIH units (National Institute of Health).

Apart from the coagulation enzymes fibrinogen and thrombin, the sheet material according to the invention may comprise further substances influencing the coagulation of the blood. These include e.g. fibrinolysis inhibitors which prevent the redissolution of the already formed fibrin clot. Suitable fibrinolysis inhibitors are e.g. antiplasmins, such as aprotinin, $\alpha_2$-antiplasmin, $\alpha_2$-macroglobulin and/or trypsin inhibitor. Furthermore, phospholipids, obtained e.g. from cerebral matter or a thrombocyte preparation, may be added. Besides, for the specific treatment of haemophilia, there may be provided an increased offer of the factors VIII and/or IX. Moreover, factors may be added which are conducive to the spreading-in and the growth of fibroblasts and thus speed up the healing of the wound. For this purpose, there may e.g. be provided a low content of fibronectin.

According to a preferred aspect of the invention at least one layer of the sheet material—preferably one or both thrombin-containing outer layer(s)—contains fibroblast cells which are present in dry state and of which at least a fraction may be reactivated. Fibroblasts are elongated, spindle-shaped cells with long cell processes. They occur in the loose connective tissue, where they form the collagenous as well as elastic fibers. For the present invention, fibroblasts of human origin which have been reproduced by cell division in suitable nutrients come into consideration. For example, fibroblasts may be isolated from juvenile, mesenchymal tissue and slightly be reproduced by cell division in a basal medium according to "Eagle" of the company Böhringer, Mannheim, with an addition of bovine serum albumin. The fibroblast cells are separated from the culture broth by centrifuging and washed with 0.9% of NaCl solution. Thereupon, the fibroblast cells freshly obtained in this case may be added to the selected glycoprotein solution and/or suspension for producing a predetermined sheet-material layer. Alternatively, the freshly obtained fibroblast cells may be suspended in a protein-containing solvent and this suspension may be deep-frozen until further use.

The freshly obtained fibroblast cells or the fibroblast cells stored in deep-frozen state are added to the glycoprotein solution and/or suspension used for the production of a predetermined sheet-material layer in such an amount that the finished dry sheet material contains $10^3$ to $10^{10}$ fibroblast cells in dry state per 1 cm$^3$ of the glycoprotein matrix. An amount of approx. $10^4$ to $10^6$ fibroblast cells in dry state per 1 cm$^3$ of glycoprotein matrix of the finished dry sheet material is particularly preferred.

It has been found within the scope of the present invention that at least 10%, mostly 15% and more, of the fibroblast cells which after deep-freezing and lyophilization are present in dry state in the dry sheet material may again be reactivated even after prolonged storage of the sheet material at room temperature when contacted with human serum and will spread into the wound area as well as into the substrate offered with the sheet-material. Thus, when mention is made in these papers (specification and claims) of "fibroblast cells present in dry state", the term "fibroblast cells present in dry state" shall be understood to refer to and describe such peripheral conditions, e.g. in the isolation, separation and, where applicable, storage of the fibroblast cells, in the preparation of the sheet-material layer and in the finishing, sterilization and storage of the dry sheet material where from the total number of the dry fibroblast cells presents at least 10% and preferably 15% or more may again be reactivated when contacted with human serum.

Besides, it has been found that also the presence of non-reactivatable fibroblast cells in the sheet material according to the invention may have a favourable influence, presumably through the increased offer of certain proteins, enzymes, active substances and factors.

The composition of the interstitial tissue is effected by polyanionic glycosamine glycans. These include the chondroitin sulphates A, B and C (chondroitin sulphate C=dermatane sulphate) and the keratane sulphate as well as the sulphate-free hyaluronic acid. Glycosamine glycans are polymeric carbohydrates (mean molecular weight mostly between 6,000 and 12,000), which usually contain sulphate and acetate groups in addition. These glycosamine glycans bond proteins so that proteoglycans are formed, which, in their turn, may associate hyaluronic acid. Thus, the endogenous connective tissue is formed, into which the fibroblasts spread.

According to a further aspect of the invention there is provided in at least one layer of the sheet material a content of these agents which are specifically conducive to the growth of the fibroblasts and their spreading-in. Especially chondroitin sulphate, the commercially available chondroitin sulphate mixture (chondroitin sulphate A and B), dermatane sulphate (chondroitin sulphate C), keratane sulphate and hyaluronic acid come into consideration as such agents. The use of chondroitin sulphate is especially preferred. Preferably, the proportion of these agents conducive to the growth of the fibroblasts and their spreading-in, especially of chondroitin sulphate, shall amount to 0.1 to 1 mg per 1 cm$^3$ of the glycoprotein matrix of the finished dry sheet material. The specified agents, such as chondroitin sulphate, condroitin sulphate mixture, dermatane sulphate, keratane sulphate and hyaluronic acid are commercially available and may e.g. be obtained from the companies FLUKA, Fein-Che-mikalien GmbH, Neu-Ulm, Federal Republic of Germany, or SIGMA, Munich, Federal Republic of Germany.

A content of these agents conducive to the growth of fibroblasts and their spreading-in, especially of chondroitin sulphate, promotes to the growth and the spreading-in of the living fibroblasts carried along with the serum in the wound area and therefore is appropriate also without an additional offer of fibroblast cells present in dry state. However, the joint presence of these agents conducive to the growth of the fibroblasts and their spreading-in, here especially chondroitin sulphate, and of dry-state fibroblast cells in the dry sheet material is particularly preferred—and here preferably in at least one of the thrombin-containing outer layers.

Further, salts may be added, such as e.g. NaCl, CaCl$_2$, buffer salts, such as carbonate or the like, which remain in the matrix, activate the coagulation factors and, where applicable, increase the solubility of the glycoproteins.

The contact layer, viz. the thrombin-containing layer, preferably contains additionally adrenaline and/or ergotamine. Both substances are vasoactive, which has the consequence that the blood coagulates more quickly. Preferably, 0.05 to 0.1 mg of adrenaline per 1 cm$^3$ of glycoprotein matrix are provided; regarding the ergotamine there is preferably provided an amount ranging from 0.5 to 10/$\mu$g per 1 cm$^3$ of the glycoprotein matrix.

If antibiotics are provided, such as e.g. gentamycin (a known broad spectrum antibiotic), the same preferably shall also be contained in the thrombin-containing layer. The fibrinolysis inhibitors may be provided in all layers, but preferably are contained in the fibrinogen-containing layer.

In the following the invention will be explained in detail by means of preferred embodiments with reference to the drawings, in which FIG. 1 shows a double-layer embodiment of the sheet material; and FIG. 2. shows a three-layered embodiment of the sheet material.

According to one embodiment, the sheet material according to the invention is double-layered and consists of a thrombin-free layer, in the glycoprotein matrix of which the fibrinogen is distributed substantially homogeneously, as well as of the fibrinogen-free layer, in the glycoprotein matrix of which the thrombin is distributed substantially homogenously. The glyco-protein matrix of the respective layers may be made of the same or of different glycoproteins.

Such an embodiment is schematically shown in FIG. 1, where the thrombin-free layer is referenced 1 and the fibrinogen-free layer is referenced 2.

With such a double-layer embodiment it is possible to conform the thrombin offer specifically to the wound area to be treated, for instance, to provide for heavily bleeding wounds a high thrombin offer for rapid haemostasis while the additional fibrinogen offer is small.

The thrombin-containing layer is intended for application onto the wound, and for this purpose it is suitably marked, for instance dyed with haemoglobin.

Preferably, each layer 1 and 2 is of foam or fleece structure. Due to its large surface, this structure ensures a good absorptive capacity. The increased contact area activates the coagulation factors contained in the flow of blood as well as the factors additionally offered with the sheet material. A fleece formed of glycoprotein fibers has an even greater mechanical stability than a corresponding foam structure; this may be of importance, for instance, in the treatment of muscle lacerations.

For each layer of the double-layer structure preferably a layer thickness of approx. 1 to 5 mm is provided. This range of the layer thickness may rapidly be soaked by the flow of blood so that the coagulation factors offered with the sheet material are rapidly activated.

According to a further embodiment, the sheet material according to the invention may be three-layered. Such an embodiment is schematically shown in FIG. 2, where the centrally disposed layer is referenced 4 and the two outer layers are referenced 3 and 5.

In such a three-layered structure preferably the fibrinogen is contained in the centrally disposed layer 4 and the thrombin is contained in at least one of the two outer layers 3 and 5. In some cases of application, for instance, in the case of sheet materials which are to be applied in the abdominal cavity, e.g. for treating intestinal sutures, it may be suitable to cover the centrally disposed fibrinogen-containing layer on one side with a thrombin-containing layer and on the other side with a layer which is free both from thrombin and from fibrinogen but contains coagulation-inactive proteins, such as albumin or globulin. This prevents reliably that the resultant fibrin networks lead to an adhesion of the intestinal loops.

In a further embodiment of the three-layered sheet material thrombin is contained in both outer layers. This embodiment is mainly suited for the treatment of deeper muscle lesions or ruptures of soft organs (liver, spleen, pancreas), because the thrombin layer on either sides causes rapid closure of the numerous open capillaries in the mentioned organs. These thrombin-containing wound materials may be used advantageously also in the case of more heavily bleeding surgical wounds, such as those frequently occurring in gynaecology or orthopaedics. The thrombin-containing layers, which are intended for direct contact with the wound, need not be marked particularly. When placed into the wound gap, both sheet material surfaces react with the adjacent wound surface.

In the three-layered structure, preferably a greater layer thickness is provided for the central layer 4 than for the two outer layers 3 and 5. This permits forming the centrally disposed, fibrinogen-containing layer 4 of such glycoproteins as are incorporated directly into the fibrin network and, as a rule, only have a low mechanical strength, such as e.g. fibrin fission products. It is thereby possible to control the mechanical stability of the wound closure under load. The mechanical strength may be further increased by the additional presence of collagen and/or modified collagens. The greater the offer of fibrinogen per unit of area of the central layer 4, the more fibrin will be formed, which, in its turn, increases the mechanical stability of the wound closure under load.

Figure 2:
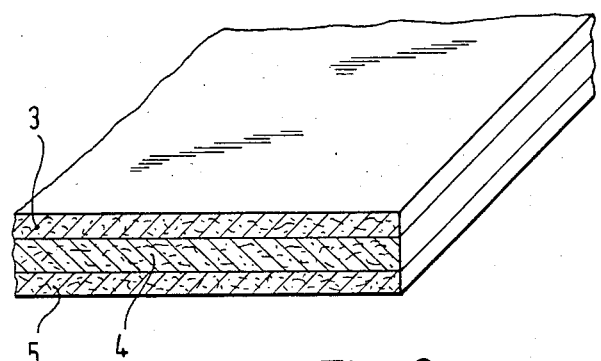

According to a further embodiment of the invention, the single-stratum central layer 4 shown in FIG. 2 may be replaced by two or more individual layers, which results in a four-layered or even more-layered structure, wherein the composition of the inner layers may be matched to predetermined applications, for instance, a delayed release of active substance and accordingly an extended influence on the healing of the wound may be achieved. For example, it is possible to provide between the outer contact layers a number of layers having different active-substance contents, which, when dissolving, release the substances contained therein into the wound area in a graduated order relative to time. Such an embodiment is recommendable, for instance, for the treatment of infected bone fractures, to which antibiotics have to be supplied for a prolonged period of time, which then are released in a graduated order relative to time due to the different decomposition rates of the layers.

Regarding the optimum composition of the sheet material according to the invention, especially the following aspects are applicable:

The dissolution rate of the glycoprotein support material determines the field of use of the fibrinogen fleece. Where a long residence time of the wound closure material is desired, collagen must be used as a support material. Where only a rapid closure of the wound is to be achieved, but the material is to be decomposed rapidly by endogenous proteases, recourse must be taken to other plasma proteins (albumin, globulin, fibrin).

Therefore, an optimum composition shall start with thrombin-containing outer layers.

For this purpose, albumin or globulin are suited as support materials (in dry form).

Small additions of collagen increase the mechanical stability in this layer.

An additional content of fibroblast cells present in dry state and/or of agents conducive to the growth of the fibroblasts and their spreading-in, and here especially chondroitin sulphate, in at least one of the thrombin-containing outer layers promotes the healing of the wound.

The fibrinogen-containing layer shall be disposed centrally, whereas the following outer side must not comprise anything but thrombin or covering, coagulation-inactive proteins such as albumin or globulin.

In a particularly preferred embodiment of the sheet material, the outer layer consists of a thrombin-containing layer (made of an aqueous 5% albumin solution containing 200 to 1,000 units of thrombin per 1 ml) having a thickness of approx. 2 mm. The following collagen support material contains the fibrinogen. This layer is obtained by deep-freezing from an aqueous, saline collagen solution with 1 mg fibrinogen per ml of solution. The collagen content, which mostly is within the range from 0.8% to 2.0%, may be lowered to a final concentration of 0.25% provided a fibrin suspension or another plasma protein is additionally added as a stabilizer. The second outer layer is formed by albumin from a 5% aqueous solution. When required, thrombin is added also to this outer layer.

The invention is further explained by the following examples, which, however, do not constitute a limitation thereof.

EXAMPLE 1

To a commercially available (company Pentapharm, Basel, Switzerland) collagen solution containing 1% of collagen in saline water 0.5 mg of solid, microcrystalline fibrinogen (obtained according to the above-described process) as well as 10 mg of solid albumin are added, per 1 ml of solution respectively. Agitation is carried out at room temperature for several minutes until fibrinogen and albumin have dissolved entirely.

This solution is poured into a flat inert dish having a plane bottom until a liquid layer having a thickness of 3 mm is obtained. Thereupon, deep-freezing takes place; for this purpose, the dish including its content is kept at a temperature of −40° C. for approx. 45 min.

Thereupon, so much thrombin-containing collagen solution is poured onto the surface of the resultant ice layer that again a liquid/ice layer having a thickness of approx. 2 mm is formed. For pouring, this second solution suitably is at room temperature. Thus, the previously formed ice layer melts on the surface, and after the renewed deep-freezing, followed by a lyophilization, a very stable bond between the layers is obtained without occurrence of an appreciable reaction of the fibrinogen due to the low temperatures and the short reaction period. For forming this second solution, thrombin ("Topostasin" of Hoffmann LaRoche, Grenzach, Baden) was dissolved in the above-mentioned (however, fibrinogen-free) collagen solution (200 units of thrombin per 1 ml of solution). Deep-freezing is carried out again; for this purpose a temperature of −40° C. is maintained for approx. 45 min. Thereupon, lyophilization is carried out under the usual conditions.

After termination of the drying operation, the sheet material is carefully loosened from one edge of the mold bottom and thereupon pulled off in the form of a shred of material. A large-area, supple, flexible protein fleece having a layer thickness of approx. 5 mm is obtained. The shred of material is deposited on an Al foil for a short time, cut to the desired dimensions, the resultant pieces are put into a recessed mold of synthetic material and the latter is closed with an Al foil. Thereupon, the package including its content is sterilized with X-rays (dose: 3,000 rad for 3 min.).

At room temperature, the resultant product has a substantially infinite storage stability without any appreciable loss of activity. For application, the package is opened and the doublelayer sheet material is placed with slight pressure onto the bleeding wound with the thrombin-containing layer in direct contact with the same. The sheet material rapidly resorbs the blood and/or plasma issuing from the wound and very rapidly causes the same to coagulate—depending on the escape of blood in the wound area, at any rate, within 3 to 5 min., wherein the sheet material turns red and forms a stable fibrin/collagen cake on the wound area.

EXAMPLE 2

A further, double-layer sheet material is produced in a way substantially analogous to that of example 1. In contrast to example 1, an aqueous, saline (0.9% of NaCl, 0.025 molar of $CaCl_2$) 5% albumin solution, to which 100 units of thrombin (Topostasin), 50 units of prothrombin (PPSB preparation of the company Immero AG, Vienna), 1,000 units of gentamycin as an antibiotic are added per 1 ml, is used to form the thrombin-containing layer. Furthermore, some crystals of haemoglobin are added to the solution as a whole so as to mark the contact layer. This solution is poured up to a layer depth of 2 mm into the mold and is subjected to deep-freezing (−40° C.). A 1% aqueous collagen solution comprising 3 mg of fibrinogen per 1 ml is poured up to a layer depth of 3 mm onto the resultant ice layer, deep-freezing is applied again, whereupon lyophilization is carried out.

EXAMPLE 3

The production of a three-layered sheet material takes place in a way which is substantially analogous to that of example 1. 50 units of thrombin are added to an aqueous 3% albumin/0.5% collagen solution, per 1 ml thereof. The solution is poured up to a layer depth of 2 mm into a mold having an inert surface and subjected to deep-freezing (−40° C.). A 1% collagen solution comprising 3 mg of fibrinogen and 2 mg of aprotinin (as a fibrinolysis inhibitor) per 1 ml of solution is poured up to a layer depth of 4 mm onto the frozen layer and deep-freezing is also applied. Finally, the above albumin/collagen/thrombin solution is again applied up to a layer depth of 4 mm, and after deep-freezing the mold, which is provided with three layers, is lyophilized. The resultant dry sheet material is lifted at one side under exclusion of moisture, loosened from the mold by means of a blunt spatula and after cutting to the specified size sealed in the packaging foil and the package including its content is sterilized.

EXAMPLE 4

Thrombin is introduced into a 5% human globulin solution (1,000 units of thrombin per 1 ml of solution) and this solution is subsequently foamed with nitrogen gas.

The foamy material is poured into the lyophilization mold and subjected to deep-freezing. The height of the layer is approx. 3 mm.

A fibrinogen-containing collagen solution (10 mg of fibrinogen and 0.075 mg of adrenaline (commercially available preparation) in 1 ml of 1% collagen solution respectively) is applied without foaming and up to a layer height of 5 mm onto the thrombin-containing layer and also subjected to deep-freezing. The final layer is formed from the above thrombin-containing 5% human globulin solution, which is applied as a foam up to a total height of 8 mm. After lyophilization, the material is cut to shape and packaged. After packaging, sterilization by radiation is carried out.

EXAMPLE 5

Non-linked fibrin is pulverized and suspended in an amount of 0.6 g per 1 ml of water. 1% of human albumin is added as an admixture. Thrombin is added in an amount of 300 units per 1 ml. The fibrin-albumin-thrombin suspension is poured up to a level of 2 mm into a mold and immediately subjected to deep-freezing. A 1% collagen solution comprising 1 mg of fibrinogen per 1 ml and 1 mg of fibrin particles per 1 ml is poured up to a layer depth of 4 mm onto the ice layer. Finally, the above thrombin-containing albumin-fibrin suspension is applied onto the deep-frozen second layer, subjected to deep-freezing and the multi-layered frozen material is lyophilized.

The removable dry protein substance forms a stable sheet material, which may be cut easily.

When used as a material which is applied on wounds, it may easily be manipulated, may be bent, which is necessary especially in the treatment of intestinal sutures, and absorbs blood or plasma in the wound area.

EXAMPLE 6

The following solutions/suspensions are used to produce a four-layered sheet material—substantially in a way which is analogous to that of example 1:
  (a) 50 units of thrombin per 1 ml of 5% aqueous, saline albumin solution;
  (b) 50 units of prothrombin per 1 ml of a 2.5% aqueous albumin solution;
  (c) 2 mg of fibrinogen, 5,000 units of gentamycin, 8/µg of ergotamine, 10,000 units of $\alpha_2$-antiplasmin, 10,000 units of $\alpha_2$-macroglobulin per 1 ml of 5% aqueous albumin solution;
  (d) 2.0% aqueous collagen solution with addition of 5,000 units of gentamycin per 1 ml of solution.

For producing the sheet material, the solution "a" is poured up to a layer depth of 2 mm into a mold having an inert surface and subjected to deep-freezing. The solution "b" is poured thereon up to a layer depth of 2 mm, the solution "c" is poured thereon up to a layer depth of 2 mm and finally the solution "d" is poured thereon up to a layer depth of 4 mm, after deep-freezing of the respective preceding layer. The finished thawed dry preparation has a compressible fleece structure with a substantially stable area and a total layer thickness of approx. 10 mm. The formation of multiple layers permits the introduction of various reactants or drugs so that, when infectious wound areas are treated, the antibiotics are released with delay and a longer protection against infections is ensured. Collagen in the soluble form, as used in the preparation of this product, is identifiable in the healing wound area for more than 14 days. Within this period of time, the drugs offered in combination with the sheet material diffuse into the surrounding tissue. The diffusion rate is determined by the association e.g. of the antibiotic with the collagen support material or fibrin.

EXAMPLE 7

Substantially example 1 is repeated; however, additionally fibroblast cells are added to the thrombin-containing collagen solution.

Fibroblast cells originating from juvenile, mesenchymal human tissue were cultured in basal medium according to "Eagle" of the company Böhringer, Mannheim, Federal Republic of Germany, to which additionally bovine serum albumin had been added. These fibroblast cells were separated from their nutrient medium by centrifuging, washed with 0.9% of NaCl solution and thereupon taken up in a 5% human albumin solution and suspended without destruction of the cells.

Such a proportion of this fibroblast suspension is added to the solution used in example 1 and obtained by dissolution of "Topostasin" in a saline 1% collagen solution that the thrombin-containing collagen solution contains $10^3$ to $10^6$ fibroblast cells per 1 ml of collagen solution. Finally, this collagen solution containing thrombin and fibroblasts is poured onto the already form ice layer of fibrinogen-containing collagen solution and, without foaming, subjected to deep-freezing. Subsequently, both layers are jointly lyophilized, cut, packaged and sterilized. In order not to harm the fibroblast cells, the sterilization is carried out at a lower dose for a prolonged period of time, e.g. 1000 rad for 9 min.

EXAMPLE 8

Substantially example 7 is repeated; however, additionally chondroitin sulphate is added to the solution containing thrombin and fibroblasts.

In particular, a saline 1% collagen solution is so enriched with fibroblast cells obtained by centrifuging from their culture broth that 1 ml of solution contains approx. $10^3$ fibroblast cells. Thereupon, commercially available chondroitin sulphate mixture (chondroitin A and B, mean molecular weight approx. 8,000, obtained from the company FLUKA Feinchemikalien GmbH, Neu-Ulm, Federal Republic of Germany) is added in an amount of 1 mg per 1 ml of solution and dissolved. Thereupon, 30 units of thrombin per 1 ml of solution are added.

This solution is applied with a layer thickness of 3 mm onto a preformed ice layer of fibrinogen-containing collagen solution (3 mg of human fibrinogen per 1 ml of saline 1% collagen solution) and deep-frozen. Subsequently, both layers are jointly lyophilized, cut, packaged and sterilized.

EXAMPLE 9

A three-layered sheet material is produced in a way substantially analogous to that of example 7.

Fibroblast cells are separated by centrifuging from their culture broth and suspending in a saline 1% albumin solution. After adjustment of a concentration of $10^5$ fibroblast cells per 1 ml of solution, 0.3 mg of chondroitin sulphate and 300 units of thrombin—each per 1 ml of solution—are added. The resultant first suspension is poured up to a layer thickness of 4 mm into a flat 3.5×8 cm mold and deep-frozen therein.

For preparing the central layer, fibrinogen (5 mg per 1 ml of solution) is taken up in saline, 1% collagen solution. This second solution is poured onto the ice layer of the first suspension and also subjected to deep-freezing.

For producing the other outer layer, the above-mentioned first fibroblast suspension is again used in an albumin solution containing thrombin and chondroitin sulphate.

After renewed deep-freezing and the joint lyophilization, a three-layered sheet material having a total layer thickness of 12 mm is obtained.

What is claimed is:

1. A resorptive sheet material for closing and healing wound(s) consisting essentially of a glycoprotein matrix containing substances which cause and respectively, are conducive to the coagulation of blood, including fibrinogen and thrombin, wherein the sheet material is dry and of multi-layered structure; at least one layer is free from thrombin and contains in the glycoprotein matrix thereof, the fibrinogen in a substantially homogeneously distributed form; and at least one further layer is free from fibrinogen and contains in the glycoprotein matrix thereof, the thrombin in a substantially homogeneously distributed form and said thrombin containing layer is to be applied directly on to said wound(s).

2. A sheet material as claimed in claim 1 wherein at least one layer contains fibroblast cells present in dry state.

3. A sheet material as claimed in claim 2 wherein at least one layer contains in addition, an agent other than thrombin, which is specifically conducive to the growth or spreading-in, or both, of fibroblasts.

4. A sheet material as claimed in claim 1 wherein at least one layer contains in addition, an agent other than thrombin, which is specifically conducive to the growth or spreading-in, or both, of fibroblasts.

5. A sheet material as claimed in any one of claims 3 or 4 wherein the agent specifically conducive to the growth or spreading-in of fibroblasts, or both is chondroitin sulphate.

6. A sheet material as claimed in any one of claims 1, 2, or 4 wherein the sheet material is double-layered.

7. A sheet material as claimed in claim 6 wherein each layer of the double-layered sheet material has a foam or fleece structure; and each layer has a layer thickness ranging from 1 to 5 mm.

8. A sheet material as claimed in claim 3 wherein each layer of the double-layered sheet material has a foam or fleece structure; and each layer has a layer thickness ranging from 1 to 5 mm.

9. A sheet material as claimed in any one of claims 1, 2, 3, or 4 wherein the sheet material is three-layered.

10. A sheet material as claimed in claim 9 wherein the centrally disposed layer of the three-layered sheet material is free from thrombin and contains the fibrinogen in a substantially homogeneously distributed form; each outer layer is free from fibrinogen; and at least one outer layer contains the thrombin in a substantially homogeneously distributed form.

11. A sheet material as claimed in claim 2 wherein the fibroblast cells are contained in at least one of the outer layers.

12. A sheet material as claimed in any one of claims 3 or 4 wherein the fibroblast cells or the agent specifically conducive to the growth or spreading-in of fibroblasts, or both, or mixtures thereof, are contained in at least one of the outer layers.

13. A sheet material as claimed in claim 5 wherein said chondroitin sulphate is contained in at least one of the outer layers.

14. A sheet material as claimed in claim 9 wherein the glycoprotein of the centrally disposed layer differs from that of the outer layers in at least one property selected from the group of chemical identity, density, layer thickness, degree of polymerization, and stability under mechanical load.

15. A sheet material as claimed in claim 11 wherein the glycoprotein of the centrally disposed layer differs from that of the outer layers in at least one property selected from the group of chemical identity, density, layer thickness, degree of polymerization, and stability under mechanical load.

16. A sheet material as claimed in claim 9 wherein the centrally disposed layer of the three-layered sheet material is of greater layer thickness than the outer layers thereof.

17. A sheet material as claimed in claim 10 wherein the centrally disposed layer of the three-layered sheet material is of greater layer thickness than the outer layers thereof.

18. A sheet material as claimed in claim 9 wherein all layers of the three-layered sheet material have a foam or fleece structure; the centrally disposed layer has a layer thickness ranging from 3 to 8 mm; and the outer layers each have a layer thickness ranging from 1 to 3 mm.

19. A sheet material as claimed in claim 10 wherein all layers of the three-layered sheet material have a foam or fleece structure; the centrally disposed layer has a layer thickness 3 to 8 mm; and the outer layers each have a layer thickness ranging from 1 to 3 mm.

20. A sheet material as claimed in any one of claims 1, 2, 3, or 4 wherein the thrombin-containing layer contains 10 to 2,000 units of thrombin per 1 $cm^3$ of the glycoprotein matrix.

21. A sheet material as claimed in claim 1 wherein the thrombin-containing layer additionally contains at least one substance having a vasoactive effect.

22. A sheet material as claimed in claim 21 wherein said at least one substance having a vasoactive effect is selected from the group of adrenaline, ergotamine, and mixtures thereof.

23. A sheet material as claimed in any one of claims 1 or 2 wherein the fibroblast-containing layer contains $10^3$ to $10^{10}$ fibroblast cells per 1 $cm^3$ of the glycoprotein matrix.

24. A sheet material as claimed in claim 23 wherein the fibroblast-containing layer additionally contains 0.1 to 1 mg of chondroitin sulphate per 1 $cm^3$ of the glycoprotein matrix.

25. A sheet material as claimed in any one of claims 1, 2, 3, or 4 wherein the fibrinogen-containing layer contains 0.1 to 30 mg of fibrinogen per 1 $cm^3$ of the glycoprotein matrix.

26. A sheet material as claimed in any one of claims 1, 2, 3, or 4 wherein the sheet material has a length of 3 to 12 cm, a width of 1 to 12 cm and a total layer thickness of 5 to 20 mm.

27. A sheet material as claimed in any one of claims 1, 2, 3, or 4 wherein the glycoprotein is selected from the group of non-linked fibrin, a fibrin fission product, collagen, globulin, myoglobulin, casein, albumin, or mixtures thereof.

28. A sheet material as claimed in any one of claims 1, 2, 3, or 4 wherein the glycoprotein matrix is obtained by at least one of foaming or deep-freezing a substantially homogeneous, predominantly aqueous glycoprotein solution or suspension, or both, and subsequent lyophilization.

29. A sheet material as claimed in any one of claims 1, 2, 3, or 4 wherein the glycoprotein matrix forms a fleece the fibers of which are obtained by spinning a homogeneous, predominantly aqueous glycoprotein solution.

30. A resorptive sheet material for closing and healing wound(s) consisting essentially of a glycoprotein matrix containing substances which cause and respectively, are conducive to the coagulation of blood, including fibrinogen and thrombin, wherein the sheet material is dry and of multi-layered structure; at least one layer is free from thrombin and contains in the glycoprotein matrix thereof, the fibrinogen in a substantially homogeneously distributed form; and at least one further layer is free from fibrinogen and contains in the glycoprotein matrix thereof, the thrombin in a substantially homogeneously distributed form and wherein said multi-layered structure is obtained by the lyophilization of at least two different substantially homogeneous predominately aqueous solutions or suspensions, or both, containing glycoprotein each aqueous solutions or suspensions, or both, forming a layer, and said layers boned to each other by said lyophilization.

31. A sheet material as claimed in claim 30 wherein at least one layer contains fibroblast cells present in dry state.

32. A sheet material as claimed in claim 31 wherein at least one layer contains in addition, an agent other than thrombin, which is specifically conducive to the growth or spreading-in, or both, of fibroblasts.

33. A sheet material as claimed in claim 32 wherein the agent specifically conducive to the growth or spreading-in of fibroblasts, or both, is chondroitin sulphate.

34. A sheet material as claimed in any one of claims 30 or 3 wherein the sheet material is double-layered.

35. A sheet material as claimed in claim 34 wherein each layer of the double-layered sheet material has a foam or fleece structure; and each layer has a layer thickness ranging from 1 to 5 mm.

36. A sheet material as claimed in claim 32 wherein each layer of the sheet material has a foam or fleece structure; and each layer has a layer thickness ranging from 1 to 5 mm.

37. A sheet material as claimed in claim 30 wherein the sheet material is three-layered.

38. A sheet material as claimed in claim 37 wherein the centrally disposed layer of the three-layered sheet material is free from thrombin and contains the fibrinogen in a substantially homogeneously distributed form; each outer layer is free from fibrinogen; and at least one outer layer contains the thrombin in a substantially homogeneously distributed form.

39. A sheet material as claimed in claim 31 wherein the fibroblast cells are contained in at least one of the outer layers.

40. A sheet material as claimed in claim 32 wherein the fibroblast cells or the agent specifically conducive to the growth or spreading-in of fibroblasts, or both, or mixtures thereof, are contained in at least one of the outer layers.

41. A sheet material as claimed in claim 33 wherein said chondroitin sulphate is contained in at least one of the outer layers.

42. A sheet material as claimed in claim 37 wherein the centrally disposed layer of the three-layered sheet material is of greater layer thickness than the outer layers thereof.

43. A sheet material as claimed in claim 38 wherein the centrally disposed layer of the three-layered sheet material is of greater layer thickness than the outer layers thereof.

44. A sheet material as claimed in claim 37 wherein all layers of the three-layered sheet material have a foam or fleece structure; the centrally disposed layer has a layer thickness ranging from 3 to 8 mm; and the outer layers each have a layer thickness ranging from 1 to 3 mm.

45. A sheet material as claimed in claim 38 wherein all layers of the three-layered sheet material have a foam or fleece structure; the centrally disposed layer has a layer thickness ranging from 3 to 8 mm; and the outer layers each have a layer thickness ranging from 1 to 3 mm.

46. A sheet material as claimed in claim 30 wherein the thrombin-containing layer contains 10 to 2,000 units of thrombin per 1 $cm^3$ of the glycoprotein matrix.

47. A sheet material as claimed in claim 30 wherein the thrombin-containing layer additionally contains at least one substance having a vasoactive effect.

48. A sheet material as claimed in claim 47 wherein said at least one substance having a vasoactive effect is selected from the group of adrenaline, ergotamine, and mixtures thereof.

49. A sheet material as claimed in any one of claims 31 or 32 wherein the fibroblast-containing layer contains $10^3$ to $10^{10}$ fibroblast cells per 1 $cm^3$ of the glycoprotein matrix.

50. A sheet material as claimed in 49 wherein the fibroblast-containing layer additionally contains 0.1 to 1 mg of chondroitin sulphate per 1 $cm^3$ of the glycoprotein matrix.

51. A sheet material as claimed in claim 30 wherein the fibrinogen-containing layer contains 0.1 to 30 mg of fibrinogen per 1 $cm^3$ of the glycoprotein matrix.

52. A sheet material as claimed in claim 30 wherein the sheet material has a length of 3 to 12 cm, a width of 1 to 12 cm and a total layer thickness of 5 to 20 mm.

53. A sheet material as claimed in any one of claims 30, 31 or 32, wherein the glycoprotein is selected from the group of non-linked fibrin, a fibrin fission product, collagen, globulin, myoglobulin, casein, albumin, or mixtures thereof.

54. A sheet material as claimed in claim 30 wherein the glycoprotein matrix forms a fleece the fibers of which are obtained by spinning a homogeneous, predominantly aqueous glycoprotein solution.

* * * * *